(12) United States Patent
Silver et al.

(10) Patent No.: US 6,420,529 B1
(45) Date of Patent: *Jul. 16, 2002

(54) GENETIC SELECTION METHOD FOR IDENTIFYING LIGANDS FOR TRANSMEMBRANE PROTEINS

(75) Inventors: Pamela Silver; Tom Roberts, both of Cambridge; Charles Stiles, Newton, all of MA (US)

(73) Assignee: Dana-Farber Cancer Institute, Inc., Boston, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/035,233

(22) Filed: Mar. 5, 1998

Related U.S. Application Data

(60) Provisional application No. 60/039,295, filed on Mar. 7, 1997.

(51) Int. Cl.$^7$ .............................................. C07K 19/00
(52) U.S. Cl. ...................... 530/371; 530/350; 536/23.5; 435/69.7
(58) Field of Search ................................ 530/350, 371; 435/69.1, 69.7, 252.3, 254.11; 536/23.5

(56) References Cited

U.S. PATENT DOCUMENTS 5,030,576 A * 7/1991 Dull ........................ 435/69.7

OTHER PUBLICATIONS

D.J. Slamon et al., Science, 235:177–182 (1987).
S. Munro et al., Cell, 48:899–907 (1987).
M.S. Berger et al., Cancer Research, 48:1238–1243 (1988).
Y. Kozutsumi et al., Nature, 332:462–464 (1988).
M.D. Rose et al., Cell, 57:1211–1221 (1989).
K. Normington et al., Cell, 57:1223–1236 (1989).
S. Fields et al., Nature, 340:245–246 (1989).
A. Borg et al., Cancer Research, 50:4332–4337 (1990).
J.I. Nikawa et al., Molecular Microbiology, 6:1441–1446 (1992).
E. R. LaVillie et al., Bio/Technology, 11:187–193 (1993).
K. Kohno et al., Molecular and Cellular Biology, 13:877–890 (1993).
J.S. Cox et al., Cell, 73:1197–1206 (1993).
K. Mori et al., Cell, 74:743–756 (1993).
J. Gyuris et al., Cell, 75:791–803 (1993).
J. Filmus et al., Oncogene, 9:3627–3633 (1994).
H. Nojima et al., Nucleic Acids Research, 22:5279–5288 (1994).
D. Graus–Porta et al., Molecular and Cellular Biology, 15:1182–1191 (1995).
G. Schlenstedt et al., The Journal of Cell Biology, 129:979–988 (1995).
J.W. Clark et al., Int. J. Cancer, 65:186–191 (1996).
P. Colas et al., Nature, 380:548–550 (1996).
J.S. Cox et al., Cell, 87:391–404 (1996).
C. E. Shamu et al., Embo Journal, 15:3028–3039 (1996).
T.G. Ram, et al., Molecular Carcinogenesis, 15:227–238 (1996).

* cited by examiner

Primary Examiner—Yvonne Eyler
Assistant Examiner—Eliane Lazar-Wesley
(74) Attorney, Agent, or Firm—Nixon Peabody LLP

(57) ABSTRACT

A chimeric protein having an (a) IRE1 or analog cytoplasmic kinase domain, (b) a transmembrane domain, and (c) a ligand binding domain of a transmembrane protein other than IRE1 is described. This protein can be used to identify and/or screen for ligands and other molecules that interact with the ligand binding domain.

7 Claims, No Drawings

GENETIC SELECTION METHOD FOR IDENTIFYING LIGANDS FOR TRANSMEMBRANE PROTEINS

The application claims priority to provisional application No. 60/039,295 filed Mar. 7, 1997.

The present invention is directed to an improved method for identifying "orphan receptors" which involves a genetic selection for ligand-receptor interaction using a recombinant eukaryotic cell, preferably yeast, as a selection system.

BACKGROUND

Advances in molecular, cellular and viral biology have resulted in the identification of numerous transmembrane receptors. These advances have also made it possible to obtain transcripts and DNA encoding a range of proteins including putative transmembrane receptors. The identification of these receptors and putative receptors makes it possible to identify ligands that interact with these receptors permitting one to better understand the biology of those receptors and/or screen for compounds that modulate the effect of such receptors. However, an increasing problem is finding simple and accurate methods for identifying the specific ligands for each of these transmembrane receptors and putative transmembrane receptors. Those receptors for which a ligand has not yet been identified are referred to as "orphan receptors". Such orphan receptors are becoming more numerous as more DNA sequences, including DNA sequences encoding putative receptors, become available.

Identifying the actual ligand that interacts with such receptors can be extremely important as many of these transmembrane receptors are associated with important cellular functions. For example, many transmembrane receptors have kinase activity and are growth factor receptors and some have been associated with malignant transformation of cells. For instance, growth factor independence in cancer cells has been correlated with overexpression of growth factor receptors such as erbB2 in breast cancer [19]. The overexpression of erbB2 has been shown to activate the ras/MAP kinase pathway and inhibition of the activation of this pathway has been shown to correlate with decreased cellular proliferation [3,9]. Potential links between tumor-associated overexpression of the erbB2 receptor and reduced survival of primary breast cancer patients with metastatic auxiliary lymph node involvement exists [1,2,23]. However, despite the considerable interest in erbB2, the specific ligand that interacts with it has not yet been identified making it an orphan receptor.

Being able to identify the actual ligand that interacts with a receptor such as the erbB2 receptor permits not only a better understanding of the complex physiological interactions involved, but facilitates the development of better drug assays. Thus, it would be desirable to have a better means for assaying and selecting ligands for these orphan receptors.

Another difficulty that currently exists in rational drug development is being able to identify when a ligand-receptor interaction occurs.

Compounds including small polypeptides that interact with not only orphan receptors, but other transmembrane receptors are currently screened by a wide variety of different assays. However, it would be desirable to develop new and simple assays to determine where an interaction is occurring not only to select compounds that modulate receptor activity, either positively or negatively, but to have a simple means to determine optimal peptide sequences that will, for example, fit into the ligand binding site. Identifying such compounds permits more efficient design of compounds that can be used in, for example, anti-cancer or anti-viral strategies. Thus, it would be useful to have a simple method for selecting only those cells where such ligand-receptor occurs.

SUMMARY OF INVENTION

We have now discovered a simple method for identifying ligands and ligand-receptor interactions involving transmembrane proteins that form dimers, preferably homodimers, for activation. Preferably, the transmembrane protein is a transmembrane receptor having protein kinase activity, such as a transmembrane tyrosine kinase receptor.

This method uses the unfolded protein response (UPR) pathway that is present in all eukaryotic cells, and conserved through evolution in organisms as divergent as mammals and yeast. The accumulation of unfolded proteins in the endoplasmic reticulum triggers a signal that is transmitted to the nucleus and results in increased transcription of chaperone proteins and enzymes that function to induce the correct protein folding. In the yeast, *Saccharomyces cerevisiae,* two of the essential components of the UPR pathway have been identified. In the presence of unfolded proteins, the transmembrane kinase IRE1p transmits a downstream signal that activates transcription of chaperone proteins and enzymes. This signal is manifested by the binding of nuclear factors to the unfolded response element (UPRE), a 22 bp upstream activating element having the sequence:

5'-GATCTGTCGACAGGAACTGGACAGCGTGTCGAA-AAAGC-3' (SEQ ID NO:1)
3'-ACAGCTGTCCTTGACCTGTCGCACAGCTTTTTCG-AGCT-5' (SEQ ID NO:2)

The UPRE is necessary and sufficient to activate transcription of a linked promoter in response to the accumulation of unfolded proteins in the endoplasmic reticulum (ER) (Mori et al., *EMBO J* 11:2583–2593, 1992).

While the present method can be used in any eukaryotic cell that has a UPR pathway by using the IRE1/UPRE interaction or analog thereof, a preferred embodiment of the present invention involves using recombinant *S. cerevisiae* cell that contains a DNA segment encoding a IRE1/ERNI1 kinase domain fused to the extracellular domain of the receptor of interest, referred to as a chimeric receptor. Receptors of interest include, but are not necessarily limited to eukaryotic, viral, insect and mammalian receptors. Preferably, the receptor is a mammalian receptor. More preferably, the mammal is a human and the receptor is an orphan receptor. Like mammalian growth factors, IRE1 oligomerizes and is phosphorylated in trans in response to an accumulation of unfolded proteins in the endoplasmic reticulum (ER) [22]. When the appropriate ligand is secreted into the ER lumen, the chimeric receptor will oligomerize and activate the unfolded protein response (UPR) signaling pathway. Those cells where the pathway has been activated can readily be identified and selected by using a reporter system activated by the UPR signaling pathway. For example, one can use a responsive element such as the unfolded protein responsive element (UPRE) containing promoter fused to a marker gene such as LacZ [Cox, 1993]. Although the induction by the UPRE in an unfolded protein response is normally only two to four-fold because the protein is made at a high basal level, one can increase the level of induction by generating constructs containing multiple copies of the UPRE, and wherein the constitutive promoter elements of the marker genes are absent. Thus, the induction ratio would be much higher. The yeast colonies that have a UPR signal would turn blue on the Xgal indicator plates containing tunicamycin. Numerous other reporters can readily be used. For example, fusing the UPRE-containing promoter to the gene encoding the naturally green fluorescent protein (GFP) so that induction can be measured in living cells by fluorescence, thereby permitting the use of cell sorters. By this means, one can readily identify cells wherein a ligand has bound to a receptor, and induced the UPR signal. Thereafter, the cDNA encoding the putative ligand can be readily selected. In the instances where more than a single cDNA is selected, those cDNAs which actually encode a ligand which binds to the receptor can be readily resolved by transfecting individual cell lines containing the receptor with a vector containing one of the selected cDNAs encoding the putative ligand. One can then screen each of the transfected cell lines using standard methods (e.g., receptor binding assays) to identify those cells in which a ligand-receptor interaction occurs. The transfected cell can be a yeast cell of the present invention or any other cell that expresses the receptor protein.

DETAILED DESCRIPTION OF THE INVENTION

The present invention uses eukaryotic cells having a UPR pathway. In preferred embodiments, the present invention permits one to take advantage of the unique nature of single-celled eukaryotic organisms such as yeast in a method for readily identifying (a) ligands for orphan receptors, (b) compounds such as small molecules that specifically bind to transmembrane proteins that dimerize for activation and (c) compounds that will modulate the effect of transmembrane receptors that dimerize.

S. cerevisiae is the simplest eukaryote to possess all the characteristic features of mammalian cells from its highly conserved cell cycle machinery to hormone dependent differentiation pathways. However, this system also combines many characteristics similar to that of prokaryotes, for example, a relatively simple genome, rapid growth, etc. These features in combination with its unusually well understood biology and the recent complete sequencing of its genome make it an excellent system to study protein interactions.

We have discovered that one can take advantage of one of the signaling pathways of eukaryotic cells to identify and select ligands and other compounds that interact with transmembrane proteins. Specifically, the transmembrane protein is one that oligomerizes upon interaction with another compound on one surface of the membrane and becomes activated at the other side of the membrane to transmit a detectable response as a result of the oligomerization. Any transmembrane protein whose function involves the binding of a ligand, protein oligomerization and consequent signal transmission can be subjected to the methods of the present invention. The transmembrane protein can be derived from any organism including eukaryotes and viruses. In preferred embodiments, the transmembrane protein is a receptor, a receptor with kinase activity, and more preferably, a class I growth factor receptor. Preferably the protein is a mammalian protein. Still more preferably, the protein is a human protein.

We have discovered that one can construct chimeric transmembrane proteins containing the extracellular domain of, for example, a receptor fused to the cytoplasmic kinase domain of a yeast receptor, namely the IRE1/ERN1 (hereinafter IRE1) receptor.

IRE1 is involved in the Unfolded Protein Response (UPR) pathway. Accumulation of unfolded proteins in the ER induces transcription of proteins, including chaperones and enzymes that function to properly fold the proteins [12]. The IRE1 protein in yeast plays a major role in transducing the signal from the ER lumen to the nucleus [5,14].

The IRE1 gene encodes a transmembrane serine/threonine protein kinase that is located in the ER membrane with its kinase domain in the cytoplasm (or the nuclear interior) [5, 16]. IRE1 is believed to act analogously to plasma membrane receptors by transmitting a signal from the ER lumen to the cytoplasm after interaction with an appropriate ligand. Like many transmembrane receptors, for example growth factor receptors, IRE1 oligomerizes and is phosphorylated in trans in response to accumulation of unfolded proteins in the ER [22]. Analogously to the case with other receptors oligomerization results in a signaling cascade causing the activation of transcription factors in the nucleus.

The synthesis of the ER-resident proteins such as the chaperone BiP which in yeast is also known as Kar2, and protein disulfide isomerase (PDI) involved in protein folding and cellular reactions is regulated in response to cellular requirements. For example, when cells are exposed to reagents such as tunicamycin, that inhibit glycosylation, to reducing agents, or to calcium ionophores that deplete ER-calcium stores, induction of several ER-resident proteins occurs at the transcriptional level [8,12,18,20]. All of these treatments are thought to cause improper protein folding in the ER, the aforementioned UPR. A signal from the ER lumen is transmitted to the nucleus by activated IRE1 where transcription is then activated. Potential unfolded protein response elements (UPREs) have now been identified in promoters of at least six genes encoding ER-based enzymes that are induced in response to unfolded proteins [11,14,21]. The UPRE is a 22 base pair sequence. Moreover, it has been found that a single UPRE is sufficient to activate transcription in response to the accumulation of unfolded proteins when it is inserted into a heterologous promoter [Kohn et al, 1993, Mori et al, 1992].

We have discovered that one can take advantage of the signal transmitted by IRE1 to a UPRE to readily identify and select (a) ligands that bind with a wide range of orphan receptors, (b) other compounds that interact with such receptors and/or (c) compounds that modulate the response of such receptors.

This can be done by removing the ligand binding domain of IRE1 and substituting therefore the extracellular domain of the transmembrane protein under study. Preferably, the transmembrane protein is a receptor protein. Preferably, the mammalian protein is a human protein. Transmembrane receptors are well known in the art. For example, they include both receptors and oncogenes. For example, many oncogenes show some homology to genes involved in cell growth. For example, see the table below.

TABLE[1]

| CATEGORY | ONCOGENE | HOMOLOGUS CELLULAR GENE |
|---|---|---|
| Growth Factors | sis | PDGF-/2 |
|  | int-2 | FGF-like |
| Transmembrane growth factors | erbB | EGF receptor |
|  | erbB-2 (neu, HER-2) | M-CSF receptor |
|  | fms |  |
|  | ros, kit, and others |  |
| Membrane-associated tyrosine kinases | abl |  |

TABLE[1]-continued

| CATEGORY | ONCOGENE | HOMOLOGUS CELLULAR GENE |
|---|---|---|
| Membrane associated guanine nucleotide binding proteins | src family[2] fes, fps[3] K-, N- and H- ras | |
| Cytoplasmic serine-threonine kinases | raf/mil mos | |
| Cytoplasmic hormone receptors | erbA | Thyroid hormone receptor |

[1]Adapted from Druker, B.J., et al., N. Eng. J of MoL 321:1383–1392 (1982). PDGF denotes platelet-derived growth factor, FGF fibroblast growth factor, EGF epidermal growth factor, and M-CSF mononuclear-phagocyte growth factor.
[2]The family includes src, fgr, yes, lck, hck, fyn, lyn, and tkl.
[3]The subcellular location of these oncogene products is uncertain.

Putative receptors that share certain of the analogous domains have been identified. By using known techniques the DNA encoding the extracellular portion of a transmembrane protein such as a receptor protein can be substituted for the DNA encoding the ER-luminal portion of the IRE1 gene. For example, using at least the ligand binding portion from the extracellular domain of a mammalian growth factor receptor such as EGF or erbB2. In preferred embodiments, one would fuse the entire cDNA portion encoding the extracellular domain of the transmembrane protein to the cDNA encoding transmembrane and cytoplasmic kinase domains of IRE 1. In alternative embodiments, one can create a chimeric gene encoding the chimeric protein wherein at least the cytoplasmic domain of the receptor is deleted, and replaced by the cytoplasmic kinase domain of IRE1. These constructs can readily be made by those skilled in the art using known techniques based upon the present disclosure. For example, the sequence of IRE1 is well known. See for example, Mori, et al. 1993. Similarly, the general structure of most receptors and domains is well known. Convenient restriction sites are known in IRE1 and can readily be identified in the transmembrane receptors. Additionally, unique restriction sites in these genes can also be created by standard techniques. Thereafter using standard techniques one can fuse the portions together. Prokaryotic hosts such as *E. coli* are a convenient source for preparation on large amounts of chimeric genes. These chimeric receptors can be inserted in a yeast expression vector and used to either transiently transfect or constitutively transfect the yeast. In preferred embodiments, cassettes containing the desired portion of nucleic acid from IRE1 can be made wherein the extracellular portion from a transmembrane protein can readily be inserted.

A number of other promoters have also been shown to be useful for expression of various genes in yeast. For example, promoters naturally associated with the *Saccharomyces cerevisiae* genes TP11 (triose phosphate isomerase), PGK1 (phosphoglycerate kinase), PYK1 (pyruvate kinase) TKH1, TDH2, and TDH3 (glyceraldehyde phosphate dehydrogenase or triose phosphate dehydrogenase), and ENO1 (enolase 1) have been described as useful for expression of genes in yeast (Kawasaki, U.S. Pat. No. 4,599,311; Kingsman and Kingsman, U.S. Pat. No. 4,615,974; Burke et al., EPO Patent Application NO. 84300091.0) as well as the native IRE1 promoter. These promoters can be used to control expression of the chimeric protein. Typically, it is preferable to use promoters that do not result in high levels of expression of the chimeric protein, particularly when looking at identifying ligands. The reason for this is that if too high a level of chimeric protein is expressed autooligomerization may occur in the absence of ligand-receptor interaction.

In contrast, when looking for compounds that modulate—either positively or negative—the signal by the chimeric protein, then high levels of expression are preferable.

In addition to the particular examples described herein, cassettes containing cDNA encoding the extracellular domain of the receptor of interest fused to cDNA encoding the transmembrane and cytoplasmic domains of IRE1 can be constructed using a variety of methods well known to those skilled in the art. As stated above, generally, where it is desirable to identify the naturally occurring ligand of the receptor, or to screen for compounds which enhance the function of the receptor low copy number or integrating vectors will be used, and the expression of the receptor-IRE1 fusion protein will be placed under the control of the native IRE1 promoter or one which promotes the expression of the fusion protein at levels comparable to that of the IRE1 promoter. In contrast, where it is desirable to identify compounds which inhibit the action of the receptor higher levels of the receptor-Ire1 fusion can be achieved by using a high copy plasmid, by placing the cDNA under the control of a strong promoter (e.gs, GAL1, GAL10, ENO1, ENO2, ADH2, Met3, or both.

In preferred embodiments, one would use yeast cell lines wherein the native IRE1 gene has been inactivated. This can also readily be accomplished by standard techniques by those skilled in the art. (See, for example, Guthrie et al, *Methods in Enzymology*, Vol. 194, Academy Press, Inc., 1991.)

Similarly the yeast cells are transfected with nucleic acid encoding a reporter system that would respond to the activation of the chimeric protein. This can readily be done by inserting at least one UPRE sequence in the promoter of a reporter gene of interest. Procedures for the construction of suitable vectors, the stable transfection of cells and the analysis of the transfected cells for gene expression are well known in the art. See for example, Kaiser et al, *Methods in Yeast Genetics*, Cold Spring Harbor Press, 1994; Ausubel et al., *Current Protocols in Molecular Biology*, John Wiley & Sons, New York, 1989)

Generally, the reporter construct contains a reporter gene whose expression is under the control of a promoter containing at least one, and preferably at least between 2–4 copies of the UPRE sequence. The reporter gene can be selected from any gene whose protein product is readily detected, including but not limited to, those detectable by enzyme assays, fluorescence, immunoassay, drug resistance or auxotrophic selection. Examples of the numerous useful reporter genes available include lacZ, CAT, GFP, URA3, TRP2, LYS2 and HIS3.

Promoters which naturally contain one or more UPRE's are preferably be used in the reporter construction. Such promoters include the promoters that regulate KAR2, PD1, EUG1, and FKB2 (Kohn, 1993, Meri 1993; Schlenstedt, 1995). Alternatively, one or more UPRE's can be inserted into any other desirable promoter such as those described supra. The UPRE is a 22 bp sequence present in the promoters of genes that are activated by the UPR. It has been demonstrated that a single UPRE is sufficient to activate transcription in response to the accumulation of unfolded proteins when it is inserted into a heterologous promoter (Kohn et al. 1993, Mori et al. 1992). Mutational analysis has defined the nucleotides within the UPRE that are essential for its ability to activate transcription (Mori et al., supra). When one copy of UPRE is present in the promoter of the reporter gene there is typically a 4 to 8-fold increase in expression of the reporter protein upon addition of tunicamycin. However, increases of between 40–43 fold have been observed when the promoter contain 2–4 tandem copies. Reporter constructs containing UPRE elements can be prepared as described by Cox, et al, 1993; Cox and Walter, Cell 87:391–394, 1996.

Both the chimeric gene cassettes and the reporter constructs can be introduced into the yeast cell using any suitable vector. One of the advantages of the yeast based system is that a number of bacteria/yeast shuttle vectors are readily available (e.g., New England BioLabs, American Tissue Culture Corporation) which allow introduction of different copy numbers of the cDNA of interest into the cell. For example, when high levels of gene expression are desirable, yeast episomal plasmids, such as Yep24, based on the yeast two micron circle and which are replicated in the cell at high copy numbers can be used. Plasmids, such as YRp17, which contain a yeast chromosomal derived autonomous replicating sequence (ARS) can be used when intermediate copy numbers of the DNA are preferred. Alternatively, vectors (e.g., YCp50) which contain yeast chromosomal centrosome sequences are also available when it is desirable to maintain the DNA of interest at a level of only one to two copies per cell. In addition, a number of yeast integrating plasmids such as YIp5 can be used for stable introduction of the cDNA into the yeast strains containing a reporter construct because integration of the reporter construct into a yeast chromosome would minimize the need for maintaining multiple selection criteria.

Using the aforementioned vectors for the chimeric receptor and the reporter one can create transient cells or preferably, stable cell lines expressing the chimeric receptor/reporter. In either event, one can then readily use those cell lines to identify the ligand or compound of interest by a simple selection based upon looking at the reporter. Typically, when trying to identify a ligand one does so by selecting cells where the receptor has been activated. With respect to the other compounds, one can select those cells where there has been a change in the reporter as opposed to control cells. For example, one can use yeast cells where the reporter indicates the system has been activated, e.g., by high level expression of the chimeric reporter and autoactivation. Then one can identify compounds that inhibit the receptor by looking at a diminishing of the reporter.

In a preferred embodiment, the present invention is used to identify ligands for receptors. In that case the chimeric receptor has at least the ligand binding domain of the orphan receptor as part of the chimeric receptor. Preferably one uses stable cell lines expressing the chimeric receptor under the control of the IRE1 promoter and a reporter where the promoter contains at least one UPRE. One then needs to transfect the stable cells with nucleic acid segment encoding a putative ligand. This can readily be done by standard techniques. For example, using a library of cDNAs encoding proteins that could be expected to contain the ligand contained in an expression plasmid that replicates and produces mRNA extrachromosomally when transfected into yeast cells. For example, the orphan receptor erbB2 is associated with breast tissue. Thus, one would preferably use a library containing DNA encoding breast tissue associated proteins. Similarly, if the orphan receptor of interest had been identified from a brain tissue library one would expect to find the ligand for that receptor using a brain tissue library. Preparation of nucleic acid libraries such as cDNA libraries is known in the art and can readily be accomplished. Alternatively, one can purchase commercial libraries. For example, a number of libraries have been designed to express mammalian proteins, preferably human, proteins, in systems such as yeast. One would tranfect a population of yeast cells containing the chimeric receptor/reporter system with the cDNA library by standard means. For example, using plasmids containing cDNA encoding a putative ligand operably linked to a yeast promoter. As a result of the use of yeast and the reporter system disclosed herein, one can readily identify from the population of thousands of potential choices of cDNA only those cells that show activation of the UPRE. Those cells wherein UPRE has been activated demonstrate binding by the ligand to chimeric receptor are selected and plasmid DNA isolated by standard technique. DNA encoding the ligand can be isolated from the plasmid using standard techniques including PCR. If desired, selected cells can be cultivated by standard culturing techniques to large numbers. Additionally, if desired, the plasmid can then be amplified using, for example, *E. coli* and used to transfect yeast cells for a second round of screening.

In most instances this permits one to precisely identify the particular cDNA encoding the ligand. In some instances, there may be a few choices. This can be handled readily by a second selection system wherein a population of yeast cells containing the chimeric receptor UPRE reporter system are transfected by an expression vector containing cDNA encoding only a specific sequence. Alternatively, one can use other cells expressing the actual receptor of interest. By this means, ligands for orphan receptors can readily be identified.

In some preferred embodiments, passage of the ligands through the ER can be slowed by use of an ER retention sequence such as a KDEL sequence or its analog. For example, in yeast an HDEL sequence [15]. Additionally, in some preferred instances, it will be useful to have the plasmids encoding the DNAs in these libraries also contain a marker gene such as a nutrient specific marker to further assist selective growth of cells containing the cDNA of interest. This can be done by standard techniques using the information in the present disclosure.

The receptor ligand interactions that occur in the ER lumen are essentially analogous to the extracellular milieu where such interactions normally occur. Moreover, the present system isolates the receptor ligand interactions from other receptors and possible cross-talk which can confuse ligand identification. For example, we can construct a fusion gene encoding a chimeric protein containing the extracellular domain of a mammalian tyrosine kinase receptor such as an erbB2 or EGF receptor fused to the transmembrane and cytoplasmic kinase domain for IRE1. As previously mentioned, the over expression of erbB2 is associated with severity of certain breast cancers, while EGF is the canonical growth factor receptor which undergoes ligand induced oligomerization and activation. Activity is monitored by looking at induction of UPRE reporters. A positive response indicates that ligand dependent dimerization of the IRE1 cytoplasmic kinase domain has occurred. As a result of this, when trying to identify a putative ligand one must take care to ensure that low numbers of chimeric receptors are expressed. Thus, it is typically preferable in this instance to use a yeast promoter such as the IRE1 promoter in a cell where nature IRE1 expression has been knocked out. Thereafter, one looks for ligand-receptor interaction. The possibility of this interaction occurring can be increased by a variety of means. For example, by having the ligand contain an ER retention sequence such as HDEL. In one embodiment sec mutants in which transport of proteins from the ER to the golgi apparatus can be blocked can be used. These mutants are temperature sensitive and die at nonpermissive temperatures. Thus, one would select an intermediate temperature at which exit of the protein from the ER is slowed, but not stopped. This effectively would increase the length of exposure of the putative ligand to the ligand binding portion of the transmembrane protein of interest.

Any of a wide range of assays can be used to identify activation of the UPRE. For example, a reporter plasmid containing the UPRE-containing promotor fused to lacZ [5] or having a UPRE-containing promoter fused to the gene encoding HIS3. When lacz is used, colonies turn blue on Xgal indicator plates containing tunicamycin. When GFP is used, one can use cell sorters to take advantage of the fluorescence to identify positive yeast transformants. When HIS3 is used, the cell line should be a HIS3-yeast mutant, so that cells containing the reporter would be unable to grow on medium lacking histidine, except in the presence of productive IRE1 activation.

Thereafter, one would use an appropriate library such as with erbB2 and look for cells that have activated the UPRE system. As aforesaid, one can then select those cells, grow them up and then identify the putative ligand by standard techniques.

The DNA sequence of the clones that pass the above test can then be determined and compared to known sequences in various data banks. These putative ligand can then be expressed in a wide range of cells. For example, *E. coli*, yeast, baculovirus cells and radiolabeled. These labeled ligands can then be tested directly for binding to the surface of breast cancer cells such as 21MT-1 and 21MT-2 [19] known to express varying levels of erbB2 and/or to cells engineered to express only erbB2 using iodinated and/or biotinylated ligand in order to measure binding. One can use competition by the same ligand, only unlabeled, versus competition by an unrelated growth factor such as PDGF as a control. Alternatively, as mentioned above, one can express only the ligand in a yeast cell to determine if that specific ligand activates the UPRE response. Thereafter, one can confirm that identification with the appropriate cell which expresses the intact naturally occurring or recombinant transmembrane protein. In this manner, one can readily identify ligands for orphan receptors.

One can also use this system to identify compounds (aptamers) that bind to the ligand binding domain of the transmembrane protein. In such an assay, the yeast serves as a vessel in which the interaction occurs and generates the signal that alerts one to the potential interaction. For example, a protein from any organism can be expressed in yeast (the so called "bait") in conjunction with a cDNA library from any organism ("the fish"). The present method permits the rapid examination of the interaction of proteins of interest with a large number of random proteins expressed as aptamers. These aptamers can be prepared by known techniques or bought commercially as a library. For example, there are libraries of $10^8$ plasmids available (MGH & Genetics Institute) that direct the synthesis of randomly encoded 20-mer polypeptides within *E. coli* thioredoxin. The peptides are displayed as loops that protrude from the surface at the thioredoxin active sites, whereas chimeric peptide-proteins have no thioredoxin activity. Genes encoding each aptamer would be fused to an activation domain and a nuclear targeting domain, inserted into a plasmid and used to transfect the yeast cell and then screened for aptamer binding to the protein of interest by standard techniques such as those used in the standard two-way hybrid approach [4,10]. Thus, the thioredoxin-aptamer is the "prey" and the "bait" will be the extracellular domain of the protein of interest, e.g. erbB-2. While these aptamers are unlikely to induce receptor dimerization, they will identify peptides that bind to the surface of the ligand binding domain. Thus, they will readily identify ligands that can compete for ligand binding. Moreover it is possible to take the aptamer and modify such ligands, e.g. by adding different groups or altering the sequence of the aptamer to modulate receptor activation.

For example, an insert containing the cassette encoding each aptamer plasmid can be placed into a similar vector in which the thioredoxin protein scaffold is expressed in yeast with an N-terminal signal sequence and a C-terminal ER retention sequence. The protein can be expressed by an inducible promoter such as the GAL promoter. Expression of at least some of the peptides can cause an observable phenotype such as induction of UPR, slow growth, lethality and/or inhibition of UPR as opposed to the situation when a normal ligand is present. Those plasmids that create an observable phenotype can then be produced in bacteria and used to test whether the aptamer binds the transmembrane receptor directly or competes in the binding of ligand or some other interaction. Thioredoxin fusion proteins always appear to fold correctly, even when grossly overproduced in *E. coli*; inclusion bodies do not appear to form even when the protein is 40% of total *E. coli* [13].

After identifying an initial group of aptamers, an optimized set can be constructed by standard techniques such as mutagenesis so that the peptide expresses all other possible amino acids. Moreover, by appropriate screening, one can insure that the aptamer identified have a specific binding content. For example, of at least about $10^{-8}$M.

In an alternative embodiment of the above technique, one can introduce the cDNA encoding compounds or aptamers by encoding an ER signal with the compounds or aptamers directly into the ER and test the transfected cells directly for activation or inhibition of activation. This makes it possible to bypass an initial screening step and immediately obtain peptide ligands that mimic, inhibit or enhance receptor function. In these tests one would preferably use higher numbers of chimeric receptors for each observation.

Those skilled in the art will recognize, or be able to ascertain using no more than routine experimentation, numerous equivalents to the specific methods, nucleic acids, assays and reagents described herein. For example, using the information disclosed herein, one could readily identify the analogous IRE genes and UPRE elements from other yeast species such as *S. pombe* or *K. lactis*, as well as other eukaryotic systems including, but not limited to, insect and mammalian culture systems. Accordingly, such equivalents are considered to be within the scope of this invention.

REFERENCES

1. Berger, M. S., et al., *Cancer Res.* 48:1238–1243 (1988).
2. Borg, A., et al., *Cancer Res.* 50:4332–4337 (1990).
3. Clark, J. W., et al., *Int. J. Cancer* 65:186–191 (1996).
4. Colas, P., et al., *Nature* 380:548–550 (1996).
5. Cox, J. S., et al., *Cell* 73:1197–1206 (1993).
6. Cox, J. S., et al., *Cell* 87:391–394 (1996).
7. Fields, S., et al., *Nature* 340:245–246 (1989).
8. Filmus, J., et al., *Oncogene* 9:3627–3633 (1994).
9. Graus-Porta, D., et al., *Mol. Cell. Biol.* 15:1182–1191 (1995).
10. Gyuris J., et al., *Cell* 75:791–803 (1993).
11. Kohno, K., et al., *Mol. cell Biol.* 13:877–890 (1993).
12. Kozutsumi, Y., et al., *Nature* 332:462–464 (1988).
13. LaVallie, E. R., et al., *Biotech* 11: 187–193 (1993).
14. Mori, K., et al., *Cell* 74:743–756 (1993).
15. Munro, S., et al., *Cell* 48:899–907 (1987).
16. Nikawa, J., et al., *Mol. Microbiol.* 6:441–1446 (1992).
17. Nojima, H., et al., *Nucl. Acids Res.* 22:5279–5288 (1994).
18. Normington, K., et al., *Cell* 57:1223–1236 (1989).
19. Ram, T. G., et al., *Mol. Carcinogenesis* 15:227–238 (1996).
20. Rose, M. D., et al., *Cell* 57:1211–1221 (1989).
21. Schlenstedt, G., et al., *J. Cell Biol.* 129:979–988 (1995).
22. Shamu, C. E., et al., *EMBO J.* 15:3028–3039 (1996).
23. Slamon, D. J., et al., *Science* 235:177–182 (1987).

All publications and patents mentioned herein are incorporated by reference.

We claim:

1. A chimeric protein comprising
   (a) a cytoplasmic kinase domain of a yeast IRE1 protein, wherein said cytoplasmic kinase domain when activated transmits a signal to an unfolded protein response elements (UPRE) of SEQ ID NO:1 or SEQ ID NO:2 to activate transcription of a promoter linked to said UPRE,
   (b) a ligand binding domain of a transmembrane protein other than IRE1 and,
   (c) and a transmembrane domain of said IRE1 protein or said transmembrane protein other than IRE1.

2. The chimeric protein of claim 1, wherein the transmembrane protein is a viral protein or a mammalian protein.

3. The chimeric protein of claim 2, wherein the transmembrane protein is a mammalian receptor protein.

4. The chimeric protein of claim 1, 2 or 3 which further contains an endoplasmic reticulum retention sequence.

5. A nucleic acid sequence encoding the protein of claim 1, 2, or 3.

6. A nucleic acid sequence encoding the protein of claim 4.

7. The chimeric protein of claim 1, wherein the transmembrane domain is the transmembrane domain of said IRE1 protein.

* * * * *

```
                              SEQUENCE LISTING

<160> NUMBER OF SEQ ID NOS: 2

<210> SEQ ID NO 1
<211> LENGTH: 38
<212> TYPE: DNA
<213> ORGANISM: Saccharomyces cerevisiae

<400> SEQUENCE: 1
gatctgtcga caggaactgg acagcgtgtc gaaaaagc                              38

<210> SEQ ID NO 2
<211> LENGTH: 38
<212> TYPE: DNA
<213> ORGANISM: Saccharomyces cerevisiae

<400> SEQUENCE: 2
acagctgtcc ttgacctgtc gcacagcttt ttcgagct                              38
```